United States Patent [19]
Chia

[11] Patent Number: 4,796,014
[45] Date of Patent: Jan. 3, 1989

[54] DEVICE FOR DETECTING URINE IN DIAPERS

[76] Inventor: Jack T. Chia, 1247 West Wellington Ave., Chicago, Ill. 60657-4227

[21] Appl. No.: 29,700

[22] Filed: Mar. 24, 1987

[51] Int. Cl.[4] .............................................. G08B 21/00
[52] U.S. Cl. ................................... 340/573; 340/604; 604/361; 128/886
[58] Field of Search ................................ 340/573, 604; 128/138 A

[56] References Cited

U.S. PATENT DOCUMENTS

| | | | |
|---|---|---|---|
| 2,874,695 | 2/1959 | Vaniman | 128/138 A |
| 3,460,123 | 8/1969 | Bass | 340/573 |
| 3,508,235 | 4/1970 | Baisden | 128/138 A |
| 4,106,001 | 8/1978 | Mahoney | 340/573 |
| 4,191,950 | 3/1980 | Levin et al. | 340/604 |
| 4,205,672 | 6/1980 | Dvorak | 128/138 A |
| 4,212,295 | 7/1980 | Snyder | 128/138 A |
| 4,356,818 | 11/1982 | Macias et al. | 128/138 A |
| 4,539,559 | 9/1985 | Kelly et al. | 340/573 |
| 4,640,276 | 2/1987 | Jing-Sheng | 128/138 A |

Primary Examiner—Glen R. Swann, III

[57] ABSTRACT

A urine-detecting device adapted to be associated with a baby's diaper detects and signals the presence of urine after a sufficient time delay from the initiation of urination so as not to interfere with the baby's act of urination. The signal is audio and optionally with visual. The device is aiming at safety, compactness and convenience. It combines sensing means and fastening means with signalling means attached to it. A fastening means such as a safety pin with spaced apart electrical conductors on it is used to engage the device to a diaper. When urine bridges the space between the conductive a detection circuit is completed which activates the signal.

5 Claims, 2 Drawing Sheets

DEVICE FOR DETECTING URINE IN DIAPERS

BACKGROUND OF THE INVENTION

This invention relates to a device for sensing a damp condition in a baby's diaper and alerting attending persons as to such condition.

Diaper rash is painful and costly. This inventor as a parent of three who all had their share of diaper rash has considerable experience on the subject including the sleepless nights to watch them suffer. If an infant develops diaper rash on top of a nasty cold or vice versa, it means real trouble. Yet it can happen to any of them. All it takes is to sleep in wet stool-soiled diaper overnight in chilly weather. Although medications to treat diaper rash are available, they are after the fact and nothing in terms of prevention of it is on the market.

Since the discharge of stool would always be accompanied by urine while the reverse is not so, a device to detect urine in diaper would be sufficient for detecting both. And since changing soiled diapers on time to keep the skin dry and clean would eliminate the cause of diaper rash, this invention, therefore, would prevent diaper rash.

Numerous devices have earlier been disclosed for detecting and signalling the presence of urine in garments of babies and older people having medical problems. Many such devices, however, have been expensive to manufacture and uncomfortable to wear. Some have utilized rather high electrical currents, and some would be difficult to use. Most of all, although it is desirable to alert attending persons to change the infant's diaper, it is undesirable to use alerting means which will condition the infant to unnaturally interrupt or cease urination.

It is accordingly an object of the present invention to provide a urine sensing and alerting device which causes minimal discomfort to the wearer and is operable with very low electrical current.

It is another object of this invention to provide a device as in the foregoing object which is as easy to use as fastening a safety pin.

It is still another object of this invention to provide a device of the aforesaid nature for use in hospital nurseries enabling a nurse to quickly ascertain which baby's diaper needs changing.

It is a further object of this invention to provide a device of the aforesaid nature to turn off the alerting means promptly so as not to disturb others unnecessarily during the night.

It is a rather vital object of the present invention to provide a device of the aforesaid nature which does not interfere with an infant's normal urination.

It is still further object of this invention to provide a device of the aforesaid nature of safe and compact construction amenable to low cost manufacture for the benefit of common people.

These and other objects and advantages of this invention will be apparent from the following description.

SUMMARY OF THE INVENTION

The above and other beneficial objects and advantages are accomplished in accordance with the present invention by a device adapted to be associated with a baby's diaper to detect and signal the presence of urine comprising:
- (a) a specially constructed safety pin that doubles as a sensor by having insulatively installed on it diagonally a pair of spaced apart electrical conductors, connected to the electrodes inside of the container, to which the safety pin is secured in part and with which the safety pin is used to engage the device to diapers, cloth or disposable,
- (b) an electrically insulative means on the circular part of the safety pin to prevent unintentional contact of the conductors,
- (c) a rather large and reinforced plastic guard with only an one-sided opening to ensure safety and ease of operation,
- (d) a substantially rigid container fabricated of electrically insulative plastic, to which the safety pin is secured in part containing at least one battery, a pair of electrodes, a conductivity change sensor, a delay means, a signal-producing integrated circuit, a switch, a pulse circuit, a light bulb, an alerting means and interconnective conductor wires, whereby
- (e) when the conductors are bridged by urine, an electrical circuit is completed which produces a alerting signal.

The purpose of the light signal in certain embodiments of the invention is to enable a nurse in a crowded hospital ward to more quickly ascertain which baby's diaper needs changing. The purpose of the switch is for the attending person to turn off the alerting means as soon as he or she arrived so as not to disturb others unnecessarily especially during the night. And the benefit of the delay device of about two minutes of time is for the baby. For the time delay thus secured prior to the activation of the music allows the baby to complete normal urination.

When the device of this invention is intended for use with a diaper of the disposable type comprised of a thick layer of absorbent material, the safety pin is inserted and threaded through said thick layer before locked inside the guard. Thus the device as a whole does not touch the baby's skin at all.

Same benefit is applicable for use with a cloth diaper. For a cloth diaper of commercially supplied type which is also comprised of a thick layer of absorbent material in the middle, the safety pin is only threaded through said thick layer without touching the baby's skin. For a cloth diaper of home-made type which is usually in the shape of a square and when in use is folded in double into a triangle, the safety pin is inserted and threaded through the outer layer only without touching the baby's skin either, an extra feature of safety. In addition, after each use, all that needs to be cleaned is only a small portion of the safety pin, an extra feature of convenience.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
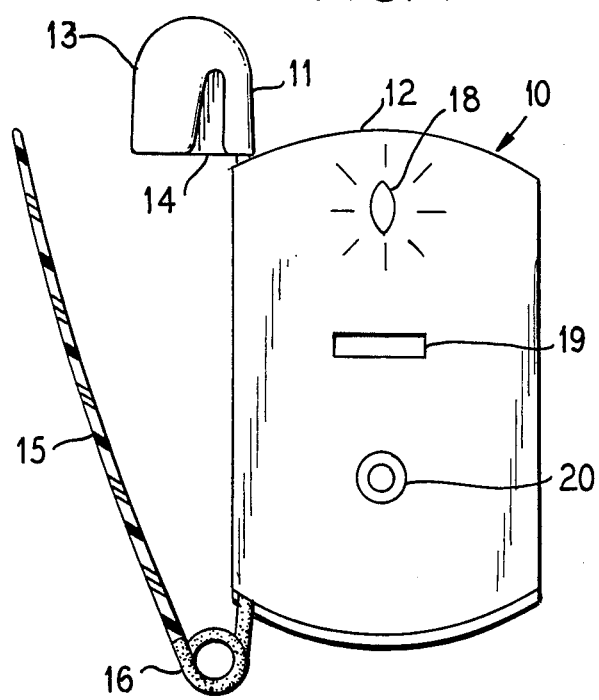
FIG. 1 is an enlarged front view of an embodiment of the device of the present invention.
Figure 2:
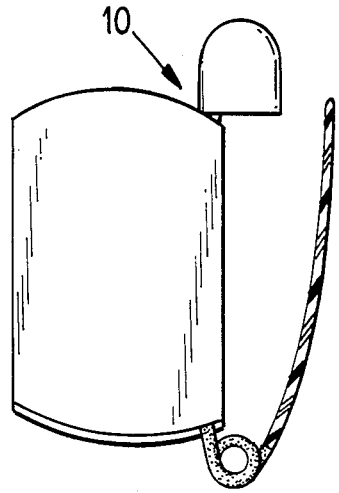
FIG. 2 is a back view of an embodiment of the device of the present invention.
Figure 3:
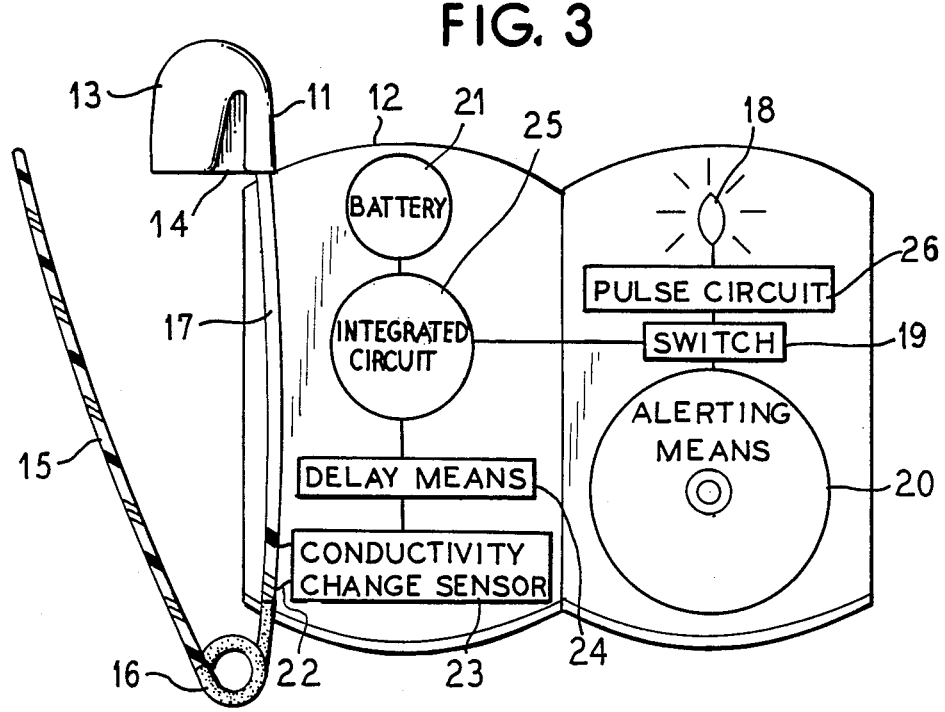
FIG. 3 is an enlarged front view of the device as FIG. 1 with its container component shown in an opened state.
Figure 4:
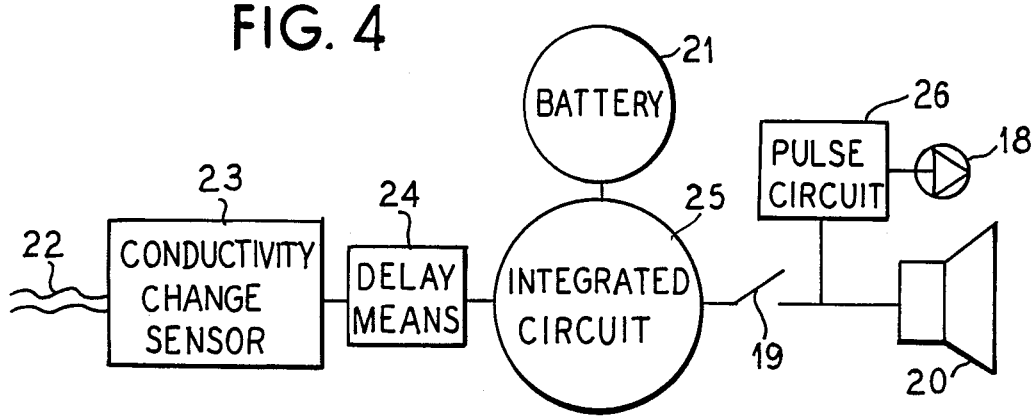
FIG. 4 is a block diagram illustrating the electrical circuitry utilized in the device.

Referring to FIGS. 1–4, an embodiment of the device (10) of the present invention, comprises a specially constructed safety pin (11) as a part of the container (12) wherein the safety pin is further comprised of a reinforced plastic guard (13) with an one-sided opening (14) on the left side of the guard, a pair of spaced apart electrical conductors (15) painted on or mounted on the pin diagonally in parallel, and an electrical insulation means (16) on the circular part of the safety pin as well as a base coat of electrically non-conductive paint on the pin to begin with.

Shown on the cover of the container are light bulb (18), switch (19) and alerting means (20).

The safety pin is secured in part to the container by the edge at such an angle that not only is there enough room for the safety pin to open and close freely but the angle also enables the container to lay flat on a diaper to which the safety pin is fastened.

The water-tight container is comprised of a reasonably rigid electrically non-conductive material. It is further selected to be inert to urine and non-iritating to skin. So is the material for the guard of the safety pin and for the electrical insulation means on the circular part of the pin. The width of the container may range between 8/10″ and 1 3/10″, the thickness from 2/10″ to 5/10″, and the length between 1 2/10″ to 1 8/10″. The size of the safety pin is ajusted to the size of the container accordingly.

Housed within the container are at least one battery (21) which may establish a 1½ volt power source or smaller, a pair of electrodes (22) connected to the electrical conductors on the safety pin, a sense conductivity change sensor (23), a delay means (24), a signal producing integrated circuit (25), a switch (19), a pulse circuit (26), a light bulb (18), a speaker (20), and interconnective conductor wires. All of which may be of and may not be limited to CMOS (complementary metal oxide silicon) electonics or in any other combination or combinations.

Figure 5:
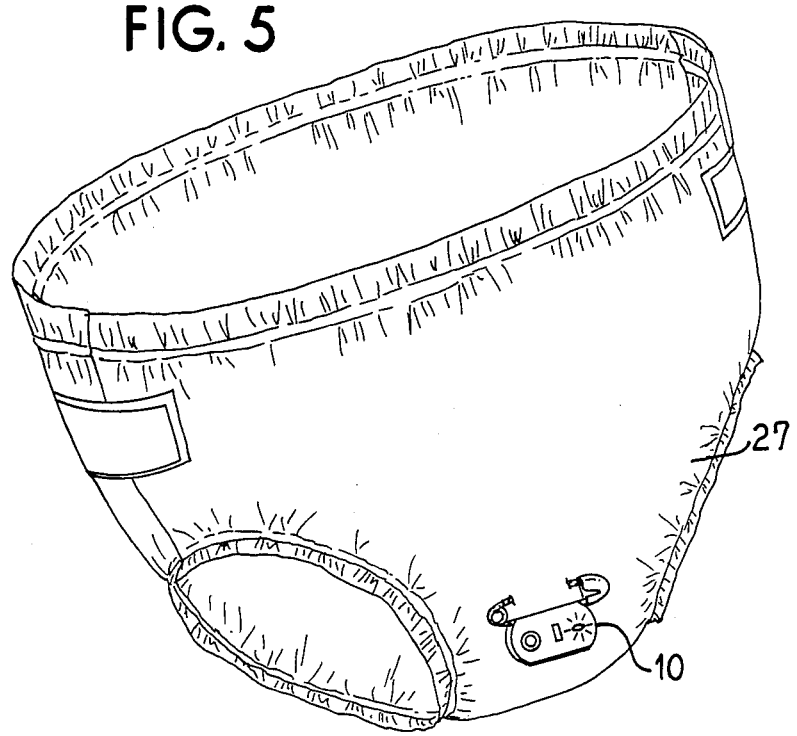
FIG. 5 is a general view of an embodiment of the device of the present invention in operative association with a disposable diaper.

FIG. 5 is a general view of the present invention in operative association with a disposable diaper (27).

In use, the device produces an audibly distinctive tune when the electrodes are bridged by urine. The nature of the tune is such as to be pleasing to the baby and distinguishable by attending persons. The tune may be programmed music and educational to infants as a subconscious head-start. The tune can be switched off at once so that it would not disturb others nearby during the night unnecessarily. Otherwise it would play to its conclusion. If the tune is programmed music and when it is turned off, it can be automatically reset and ready to play again from the beginning and such a standard mode of operation is well-known in the art.

By virtue of the specialized construction of the device with its delay device, the music signal and the optional light signal will not come on at the instant of urination, thereby avoiding interference with nature.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, I claim:

1. A compact releasably securable urine-detecting device for a baby's diaper to detect and signal the presence of urine comprising:

(a) means for sensing urine in a diaper in combination with means for fastening to a diaper,
    (b) means for signalling inside of a container,
    (c) said means for sensing in combination with means for fastening comprising a safety pin with a pair of spaced apart electrical conductors insulatively installed on it and connected to electrodes inside said container, to which said safety pin is secured and with which said safety pin is used to engage a diaper,
    (d) said container containing at least one battery, a pair of electrodes, a conductivity change sensor, a signal-producing integrated circuit, an alerting means and means for coupling them,
    (e) said safety pin being secured to said container at such an angle that not only does it allow the safety pin to open and close freely but it also enables the container to lie flat on a diaper to which the safety pin is fastened, whereby, in use, as the safety pin with electrical conductors is inserted and threaded through the front lower center of a diaper and when the conductors are bridged by urine, an electrical circuit is completed which produces an alerting signal for diaper-change.

2. The device of claim 1 further comprising a delay means in said container to postpone actuation of the alerting means for about two minutes after said conductors are bridged by urine so that the time delay thus secured allows the baby to complete normal urination without any interference.

3. The device of claim 1 further comprising a switch with its control emergent to the surface of the container so the alerting signal can be turned off once an attending person arrives so as not to disturb others nearby unnecessarily especially during the night.

4. The device of claim 1 further comprising a pulse circuit in said container and a light bulb on said container whereby when said conductors are bridged by urine and sequentially the alerting signal is activated after delay, the light will come on in an intermittant flashing manner which enables a nurse in a crowded hospital ward or an attending person in a busy cay-care center to quickly ascertain which baby's diaper needs changing.

5. The device of 1 further comprising a means for resetting said signal-producing integrated circuit so that once the signal is turned off it is automatically reset and is ready to play again from the beginning.

* * * * *